United States Patent
Tuneberg

(10) Patent No.: US 7,381,053 B2
(45) Date of Patent: Jun. 3, 2008

(54) PACKAGING SYSTEM FOR PRE-PASTED ORTHODONTIC BRACKET

(75) Inventor: Lee H. Tuneberg, Sheboygan, WI (US)

(73) Assignee: American Orthodontics Corporation, Sheboygan, WI (US)

( * ) Notice: Subject to any disclaimer, the term of this patent is extended or adjusted under 35 U.S.C. 154(b) by 166 days.

(21) Appl. No.: 11/102,547

(22) Filed: Apr. 8, 2005

(65) Prior Publication Data

US 2005/0241962 A1    Nov. 3, 2005

Related U.S. Application Data

(60) Provisional application No. 60/561,375, filed on Apr. 10, 2004.

(51) Int. Cl.
*A61C 3/00* (2006.01)

(52) U.S. Cl. .......................................... 433/9; 206/63.5

(58) Field of Classification Search .................... 433/9; 206/63.5, 368, 369, 477, 583, 460–461; 53/133.3, 133
See application file for complete search history.

(56) References Cited

U.S. PATENT DOCUMENTS

| | | | | |
|---|---|---|---|---|
| 2,793,127 | A | * | 5/1957 | Geist et al. ..................... 426/87 |
| 4,978,007 | A | | 12/1990 | Jacobs et al. ................. 206/469 |
| 5,031,786 | A | * | 7/1991 | Ingram et al. ............... 215/230 |
| 5,172,809 | A | * | 12/1992 | Jacobs et al. ................. 206/368 |
| 5,328,363 | A | * | 7/1994 | Chester et al. .................. 433/9 |
| 5,350,059 | A | | 9/1994 | Chester et al. .............. 206/63.5 |
| 5,354,199 | A | | 10/1994 | Jacobs et al. .................... 433/9 |
| 5,429,229 | A | * | 7/1995 | Chester et al. .............. 206/63.5 |
| 5,538,129 | A | | 7/1996 | Chester et al. .............. 206/63.5 |
| 5,575,645 | A | | 11/1996 | Jacobs et al. .................... 433/9 |
| 5,636,736 | A | * | 6/1997 | Jacobs et al. ................. 206/369 |
| 5,762,192 | A | * | 6/1998 | Jacobs et al. ................. 206/369 |
| 5,827,058 | A | * | 10/1998 | Kelly et al. ...................... 433/9 |
| 6,089,861 | A | * | 7/2000 | Kelly et al. ...................... 433/9 |
| 6,696,507 | B2 | | 2/2004 | Subelka et al. .............. 523/115 |
| 6,843,370 | B2 | | 1/2005 | Tuneberg ..................... 206/369 |

(Continued)

FOREIGN PATENT DOCUMENTS

JP          3-195548          8/1991

*Primary Examiner*—Cris Rodriguez
*Assistant Examiner*—Sunil K. Singh
(74) *Attorney, Agent, or Firm*—Philip G. Meyers

(57) ABSTRACT

A packaged, pre-pasted orthodontic bracket includes a container having an open well therein and a top surface surrounding the well. A cover film with a central hole is disposed over the top opening of the well and secured to the top surface of the container with a layer of adhesive. An orthodontic bracket mounted in the central hole of the cover film has a base, a central portion extending from the base, at least two opposed tie wings extending from the central portion of the bracket, and a layer of light-curable adhesive disposed on the base of the bracket. The bracket is mounted in the central hole of the cover film such that the cover film contacts the central portion of the bracket and supports the bracket with the adhesive layer and base inside the well and the tie wings outside the well. Preferably, the bracket is supported such that the layer of light-curable adhesive is spaced from a bottom wall of the well, and the cover film and the container are opaque to light in the wavelength range used to cure the light-curable adhesive.

6 Claims, 3 Drawing Sheets

U.S. PATENT DOCUMENTS

2002/0195363 A1* 12/2002 Tuneberg ................. 206/368
2003/0196914 A1* 10/2003 Tzou et al. ............... 206/63.5
2005/0167311 A1* 8/2005 Tonsfeldt et al. ........... 206/449

* cited by examiner

PACKAGING SYSTEM FOR PRE-PASTED ORTHODONTIC BRACKET

This application claims priority of Provisional U.S. Ser. No. 60/561,375, filed Apr. 10, 2004.

TECHNICAL FIELD

The invention relates to the packaging of orthodontic devices, in particular to a packaged, pre-pasted orthodontic bracket wherein the bracket is mounted in a well in a package and supported with a cover film such that the pre-pasted base of the bracket is suspended in the well.

BACKGROUND OF THE INVENTION

Modern orthodontic techniques include repositioning teeth that are misaligned, too close together or otherwise mis-positioned. In order to reposition the teeth, the teeth are connected to an arch wire that serves as a guide, urging the teeth into the desired position and orientation. In order to connect the teeth to the arch wire, small brackets with slots for receiving the arch wire are attached to the teeth. The ends of the arch wire are normally attached to the molars with another orthodontic appliance known as a buccal tube. In some cases, the bracket or tube is brazed or welded or brazed to a metal band placed around the patient's tooth. However, the preferred method of attaching brackets to a patient's teeth is by means of an adhesive. Bonding brackets to a patient's teeth is more comfortable for the patient, cosmetically more appealing and faster in practice than the use of metal bands.

Applying an appropriate amount of adhesive to the base of an orthodontic appliance such as a bracket or buccal tube can be a time consuming and tedious task for the orthodontist or his or her assistant. Too little adhesive may result in the bracket coming loose from the tooth after installation while an excessive amount of adhesive will be pushed out from between the bracket and tooth, requiring removal. Further, while two-part chemically curing adhesive systems are available for bonding orthodontic brackets to a patient's teeth, many practitioners prefer photo sensitive adhesives that are cured upon exposure to light in the visible spectrum for a relatively short period. Consequently, time is also a factor insofar as the adhesive applied to the bracket can only be exposed to visible light for a limited period before the bracket is positioned on the tooth.

In order to address these issues, pre-pasted orthodontic appliances were developed. Pre-pasted orthodontic appliances have an adhesive, normally a photo sensitive, light curing adhesive, applied to the base of the bracket before the bracket is packaged. Pre-pasted brackets reduce the amount of time required to install brackets on the patient's teeth by eliminating the need for the orthodontist to apply the adhesive to the bracket. Pre-pasted brackets also reduce the amount of wasted adhesive as the manufacturer can precisely control the amount and placement of the adhesive on the base of the bracket.

Packaging for brackets with a pre-applied light curing adhesive must protect the adhesive from exposure to light, as well as from contamination and evaporation. Further, if the adhesive adheres to the package, the adhesive coating may be disturbed when the bracket is removed from the package. Thus, in some cases, the pre-pasted portion of the orthodontic appliance is isolated from the package material with a release coating or layer. In addition, the package should present the bracket to the orthodontist in a fashion that facilitates quick and convenient removal of the bracket from the package.

SUMMARY OF THE INVENTION

A packaged, pre-pasted orthodontic bracket in accordance with the invention includes a container having an open well therein and a top surface surrounding the well. A cover film with a central hole is disposed over the top opening of the well and secured to the top surface of the container with a layer of adhesive. An orthodontic bracket mounted in the central hole of the cover film has a base, a central portion extending from the base, at least two opposed tie wings extending from the central portion of the bracket and a layer of light-curable adhesive disposed on the base of the bracket. The bracket is mounted in the central hole of the cover film such that the cover film contacts the central portion of the bracket and supports the bracket with the adhesive layer and base inside the well and the tie wings outside the well. Preferably, the bracket is supported such that the layer of light-curable adhesive is spaced from a bottom wall of the well, and the cover film and the container are opaque to light in the wavelength range used to cure the light-curable adhesive.

In one variation, a second layer of adhesive secures the cover film to the central portion of the bracket. In another aspect, the cover film has a radial slit therein extending from the central hole to an outer edge of the film, permitting the film to be wrapped around the central portion of the bracket. Thus, the film may be wrapped around the bracket such that the film extends more than 360 degrees about the central hole forming an overlapping end flap.

DETAILED DESCRIPTION

Figure 1:
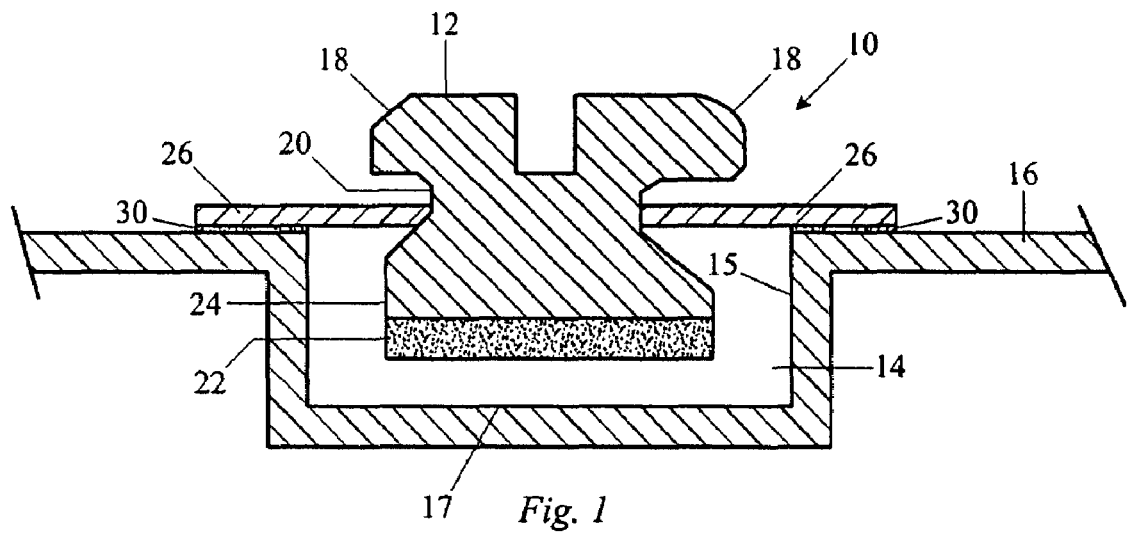
FIG. 1 is a cross section of a pre-pasted bracket package in accordance with the invention.
Figure 2:
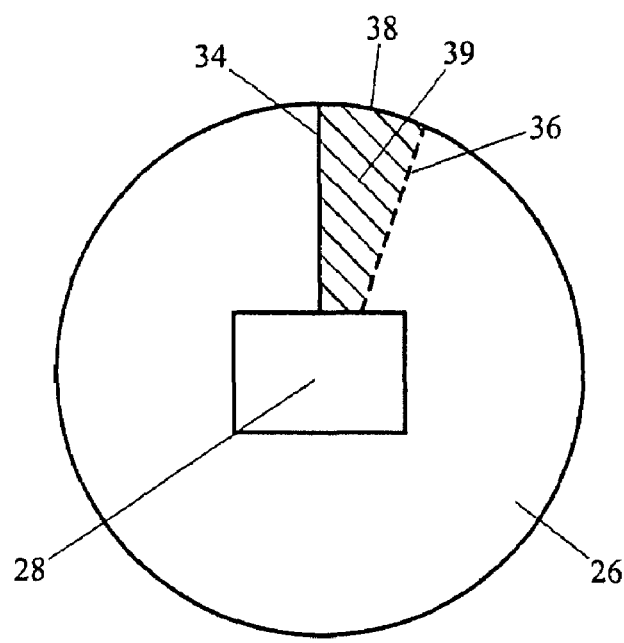
FIG. 2 is a top view of a cover film or skirt used in the container of FIG. 1.

Referring to FIGS. 1 and 2, a pre-pasted orthodontic bracket and package assembly 10 of the invention includes a bracket 12 and a container 16. Bracket 12 is supported part way inside a circular well 14 of container 16. Well 14 has a cylindrical sidewall 15 and a flat bottom wall 17. Container 16 may be vacuum formed from an appropriate plastic material such as polyethylene or an ethylene copolymer with a filler or dye that renders the substrate opaque to visible light. See commonly-assigned U.S. Patent Publication 20020195363, Dec. 26, 2002, the contents of which are incorporated by reference herein. Bracket 12 includes a pair of opposed tie wings 18, a narrowed central portion 20 and a flat base 24. A light curable adhesive paste layer 22, typically curable with visible light in the 400-510 nm wavelength range, is adhered to the bottom surface of base 24.

A circular skirt or cover film 26 formed from a thin flexible plastic film covers well 14 and supports bracket 12 in the well. Skirt 26 has a rectangular central opening 28 configured to receive bracket 12, and is adhered to the upper surface of container 16 around the periphery of well 14 with an annular pressure sensitive adhesive layer 30. In order to protect light-curable adhesive layer 22, skirt 26 and container 16 are opaque to visible light, at minimum to wavelengths effective to cure the adhesive, in this example actinic radiation in the range of 400-510 nm. If an additional cover is used as described further below, then skirt 26 may be transparent.

Bracket 12 is positioned in opening 28 such that skirt 26 encircles central portion 20 of the bracket, preferably at a location below and spaced apart from tie wings 18. Skirt 26 supports the bracket with tie wings 18 extending above container 16 and adhesive layer 22 suspended and spaced above bottom wall 17 of well 14. Thus, adhesive layer 22 is prevented from contacting container 16, avoiding the possibility that the light curable adhesive layer 22 will be disturbed by contact with the container.

Referring to FIG. 2, skirt 26 may be produced by cutting a piece of plastic film to form a circular shape with a central opening 28. Skirt 26 is slit in a radial direction forming a slit 39 such that a first end 34 of skirt 26 may overlap a second end 36 of the skirt, forming a tab 38. Since tab 38 is not in contact with pressure sensitive adhesive layer 30, a practitioner may readily grasp tab 38 with a tweezers or similar tool to peel skirt 26 away from container 16. Alternatively, the tab portion 38 may a separate piece that is applied to an otherwise circular blank used to make skirt 26. Skirt 26 could also be formed as a pair of overlapping pieces of plastic that overlap one another on opposite sides of opening 28, each half having a three-sided notch therein which form opening 28 when the two halves are superposed.

Inner edges of skirt 26 may engage central portion 20 around its periphery, causing a slight elastic deformation of skirt 26 and thereby holding bracket 12 in the position shown. For this purpose, central opening 28 has dimensions slightly smaller than central portion 20 at the location where skirt 26 engages central portion 20. Alternatively, if central opening 28 is slightly larger and engages central portion 20 at its narrowest point, mechanical engagement can be used to hold bracket 12. Given sufficient stiffness of skirt 26, bracket 12 cannot move either into or out of well 14 when skirt 26 is in place.

Figure 3:
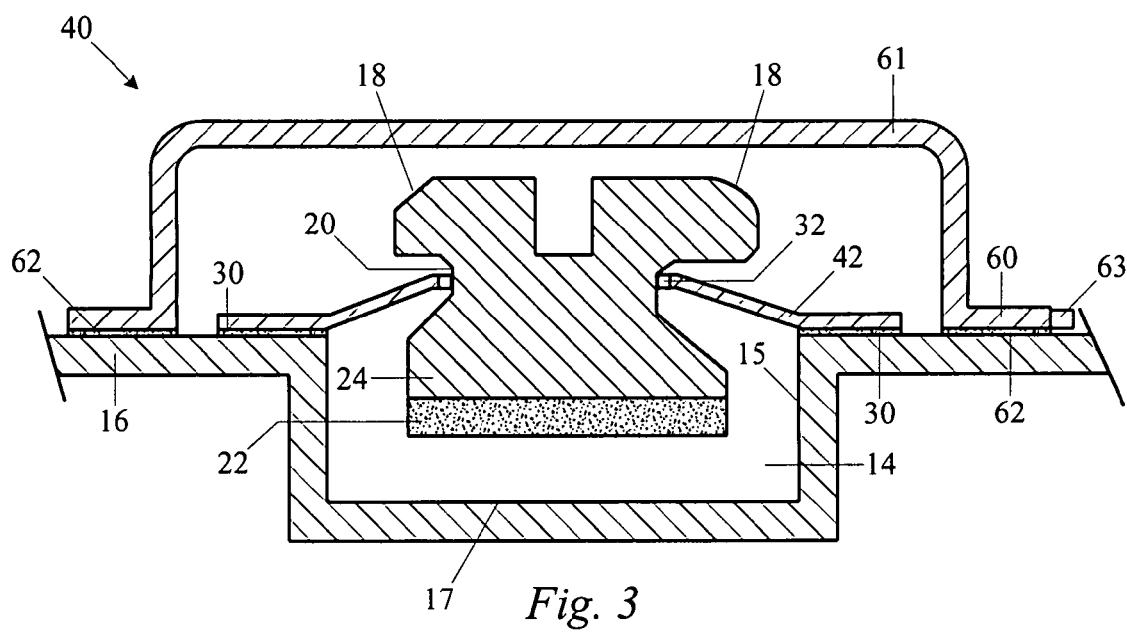
FIG. 3 is cross-section of a second pre-pasted bracket package of the invention.
Figure 4:
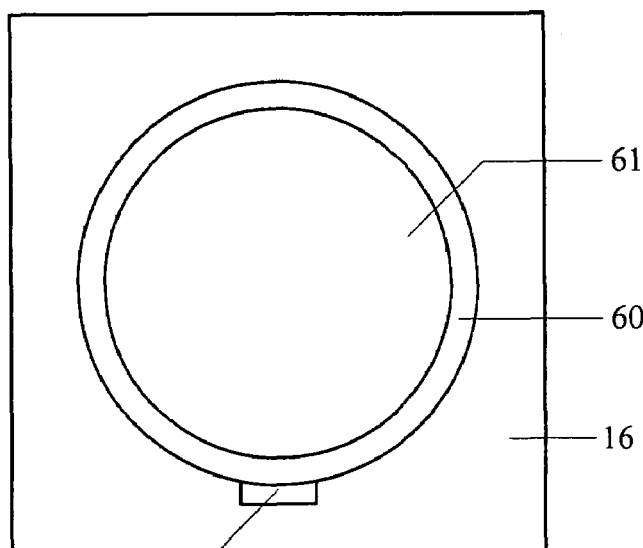
FIG. 4 is a top view of the package of FIG. 3.

Turning to FIGS. 3 and 4, in a further variation, a package assembly 40 utilizes a skirt 42 that slopes slightly upwardly from its outer perimeter to central opening 28. The sloped configuration of skirt 42 results in easier application of the skirt to container 16 and gives the skirt the shape of a truncated cone. Preferably, the slope of skirt 42 from the outside perimeter of the skirt to the edge of opening 28 is in the range of from about 0.012 to 0.015 inches per inch, or from about 0.012 to 0.015 degrees. As used herein, the term "about" refers to nominal values within normal manufacturing tolerances.

Optionally a second layer 32 of pressure sensitive adhesive is positioned around the inner periphery of skirt 42 to adhere skirt 42 to the bracket. Second adhesive layer 32 aids in sealing well 14 to prevent deterioration of paste layer 22. Preferably, layer 32 is formed on skirt 42 and is releaseably adhered to midportion 20 or bracket 12, so that no adhesive residue if left behind when skirt 42 is removed.

Packages according to the invention are preferably placed inside a secondary container providing a gas-tight seal, such as a zip-loc bag. This is especially useful if no inner adhesive layer 32 is used. In addition, one or more caps or covers may be provided over the container 16. As shown in FIG. 3, a flange 60 of a cylindrical plastic cover 61 is secured outside of skirt 42 by a third layer of pressure sensitive adhesive 62, which may comprise a radial enlargement of adhesive layer 30. A tab 63 is provided to aid in peeling off cover 61 at the time of use. Cover 61 may be made of a plastic opaque to visible light, in which case skirt 42 may be made of a transparent plastic film.

Figure 5:
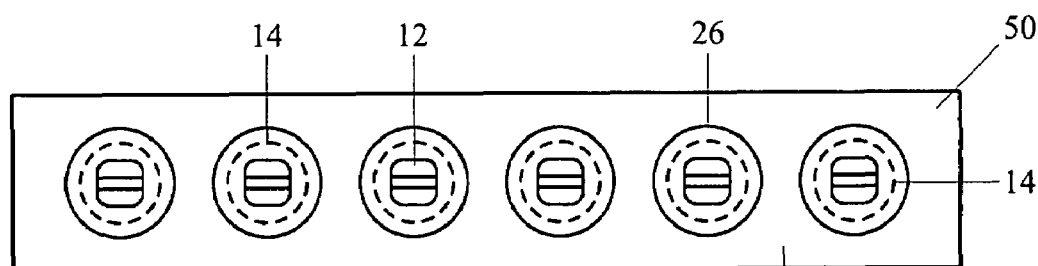
FIG. 5 is a top view, partly in phantom, of a multi-bracket package according to the invention.

Turning to FIG. 5, a package 50 for multiple orthodontic brackets comprises a plurality of circular wells 14 formed in a plastic strip 52. A plurality of brackets 12 are each supported in a well 14 by a skirt 26 as shown in FIG. 1. Package 50 is configured for six brackets 12, but the package may be configured for a greater or lesser number of brackets, depending upon the particular application and specific type of brackets, and may have more than one row of brackets.

Figure 6:
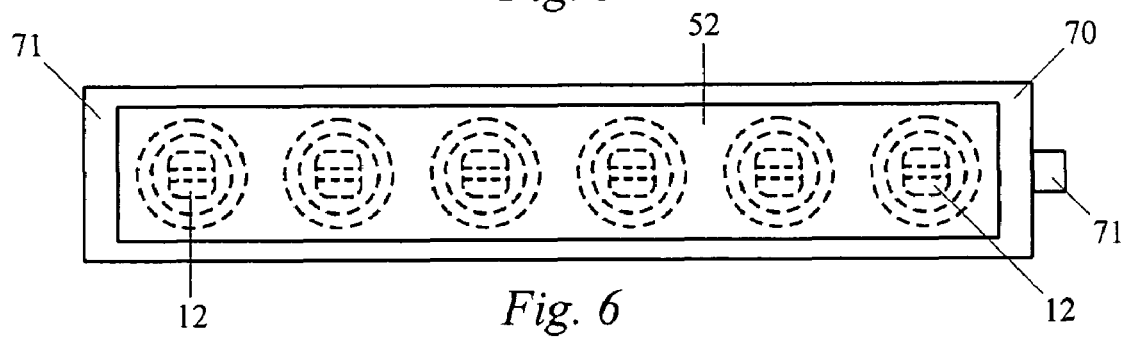
FIG. 6 is a top view, partly in phantom, of the embodiment of FIG. 5 with a cover added.

FIG. 6 illustrates an embodiment similar to that of FIG. 5 wherein a single rectangular cover 70 similar in construction to cover 61 covers all of the brackets 12 until the time of use. A removal tab 71 is provided at one end of strip 52, and a rectangular outer flange 72 of cover 70 is secured to the strip by a pressure sensitive adhesive in the same manner as cover 61.

Figure 7:
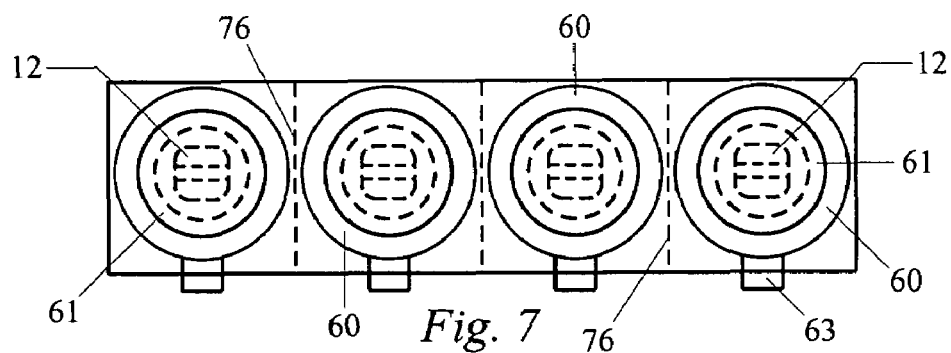
FIG. 7 is a top view, partly in phantom, of a second embodiment of a multi-bracket package according to the invention.

FIG. 7 illustrates a series of individually packaged brackets 12 using covers 61 as in FIG. 3. Containers 16 are formed in a strip with perforations 76 between each container to permit the user to remove one bracket package at a time.

While certain embodiments of the invention have been illustrated for the purposes of this disclosure, numerous changes in the method and apparatus of the invention presented herein may be made by those skilled in the art, such changes being embodied within the scope and spirit of the present invention as defined in the appended claims.

The invention claimed is:

1. A packaged, pre-pasted orthodontic bracket, comprising:
    a container having an open well therein and a top surface surrounding the well;
    a cover film disposed over the top opening of the well and secured to the top surface by a layer of adhesive, the cover film having a central hole therein;
    an orthodontic bracket having a base, a central portion extending from the base, at least two opposed tie wings extending from the central portion, and a layer of light-curable adhesive disposed on the base, wherein the bracket is mounted in the hole of the cover film such that the cover film contacts the central portion of the bracket about its entire periphery and supports the bracket with the adhesive layer and base inside the well and the tie wings outside the well, wherein the cover film has a radial slit therein extending from the central hole to an outer edge of the film, permitting the film to be wrapped around the central portion of the bracket, wherein the film extends more than 360 degrees about the central hole forming an overlapping end flap.

2. The packaged bracket of claim 1, where the layer of adhesive is spaced from a bottom wall of the well.

3. The packaged bracket of claim 1 wherein the film slopes upwardly from the container to the central hole such that the film forms a truncated cone.

4. The packaged bracket of claim 3 wherein the slope of the film is from 0.012:1 to 0.015:1 inches per inch.

5. The packaged bracket of claim 1 wherein the cover film is spaced apart from bottom surfaces of the tie wings.

6. A multi-pack of pre-pasted orthodontic brackets, comprising a plurality of packaged brackets in accordance with claim 1, wherein the container comprises a plurality of wells configured to receive a number of brackets.

* * * * *